United States Patent [19]

Gordon

[11] 4,136,683
[45] Jan. 30, 1979

[54] INTRACELLULAR TEMPERATURE MEASUREMENT

[76] Inventor: Robert T. Gordon, 4936 West Estes, Skokie, Ill. 60076

[21] Appl. No.: 777,924

[22] Filed: Mar. 9, 1977

Related U.S. Application Data

[63] Continuation of Ser. No. 670,987, Mar. 25, 1976, abandoned.

[51] Int. Cl.² ............................................. A61B 5/05
[52] U.S. Cl. .................................... 128/2 H; 128/1.3
[58] Field of Search ........................................ 128/1-3, 128/2 R, 2 H

[56] References Cited

U.S. PATENT DOCUMENTS

| | | | |
|---|---|---|---|
| 3,712,291 | 1/1973 | Freeman | 128/1.3 |
| 3,789,834 | 2/1974 | Duroux | 128/1.3 X |
| 3,877,463 | 4/1975 | Cary et al. | 128/2 H |

OTHER PUBLICATIONS

Newbower, R. S., *IEEE Trans. on Magnetics*, vol. Mag-9, No. 3, pp. 447–450, Sep. 1973.

Kaiser et al., *IEEE Trans. on Magnetics*, vol. Mag.-6, No. 3, pp. 694–698, Sep. 1970.

Gillespie, P. J. et al., *Bio-Med. Engng.*, vol. 6, No. 8, pp. 358–362, Aug. 1971.

*Primary Examiner*—Kyle L. Howell
*Attorney, Agent, or Firm*—Francis A. Keegan

[57] ABSTRACT

The process comprises introducing minute particles into the interior of the cells. These particles being injected intraveneously while suspended in an appropriate solution are of the size generally having a diameter of approximately 1 micron or less and are of a material with properties such as ferromagnetic, paramagnetic, or diamagnetic. Shortly after being absorbed intracellularly, these particles will assume the same temperature as the respective cells which they have entered. It is a well established principle that the magnetic characteristics of ferromagnetic, paramagnetic, and diamagnetic materials vary as a function of their temperature. By measuring the magnetic characteristics of these particles shortly after they have entered the cell and with proper calibration, an exact determination of the temperature of the particle and therefore of the cell, can be made.

9 Claims, No Drawings

INTRACELLULAR TEMPERATURE MEASUREMENT

This is a continuation of application Ser. No. 670,987, filed Mar. 25, 1976, now abandoned.

INTRODUCTION

This invention relates generally to a process for the exact measurement of the temperature within the cell and for the application of this process in detection and diagnosis of certain diseases such as cancer and also as instrumentation to assist in their treatment as described in Patent application Ser. No. 499,074, Dr. Robert Thomas Gordon, filed Aug. 20, 1974, abandoned and continued in application Ser. No. 651,395 filed Jan. 22, 1976.

BACKGROUND OF THE INVENTION

There are presently a number of methods and techniques for the measurement of temperature in the body. These include the various surface techniques, they include certain probes which can be inserted into particular areas and various infra-red devices such as thermography, but there are no known methods of measuring the intracellular temperature of cells in the body.

OBJECT OF THE INVENTION

It is therefore the purpose and the principle objective of the present invention to measure the intracellular temperature of cells within the body by measuring the magnetic characteristics of the particles introduced into these cells and translating this data into temperature readings.

DESCRIPTION OF THE INVENTION

The process described in this invention will make it possible, when obtained on a three dimensional basis, to construct a three dimensional model of the body or any part thereof and to show the exact temperature gradient that exists, thus greatly facilitating not only detection and diagnosis, but also treatment.

It is a well established fact that cancer cells have a higher resting temperature than do normal cells and this fact has been utilized to some extent in present cancer detection techniques; for example, in infra-red thermography which takes an infra-red picture of the body or any specific area and cancer sites will often show up as a slightly warmer area. The problem is that the effectiveness of this technique is limited to cancer cells which are at, or are near, the surface. Furthermore, since the outer membrane of cancer cells is a very effective thermal barrier, the temperature differential becomes more difficult to detect. Using the process embodied in this invention, it will not matter whether the cancer cells are near the surface or not, and the insulating properties of the cells' membrane will be completely bypassed, thus greatly facilitating true measurement readings and vastly improved cancer detection techniques.

In practice, this invention will afford patients a rapid, painless, harmless method for cancer detection. The patient will simply receive a intravenous injection of a harmless solution containing said minute particles and a short time later will enter a magnetically shielded room wherein the patient will be scanned in three dimensions by sensitive magnetic sensing equipment such as a vibrating magnetometer or a flux-gate magnetometer which will measure the magnetic characteristics of said particles which, in turn, will be calibrated to give an indication of the exact temperature of said particles. This data can then be reconstructed into a three dimensional model showing the exact temperature gradient and making possible the proper detection and diagnosis.

In the treatment process described in Patent application Ser. No. 651,395 filed on Jan. 22, 1976 by Dr. Robert Thomas Gordon, where it is desired to add an increment of heat in order to raise the temperature of the cells a specific amount, it is essential to know the exact cell temperature at all times. For example, the magnetometer equipment such as a flux-gate magnetometer will be synchronized with the high frequency electro-magnetic field generating equipment which raises the temperature of the particles so that the magnetic susceptibility measurement calibrated for corresponding temperature measurement is taken during one second interruptions in the application of this high frequency electro-magnetic field. These one second interruptions would be at 30 second intervals so that there would be continuous monitoring of the cells temperature. This data of the temperature increase in the particles obtained through the magnetometer type equipment during these one second interruptions would provide precise data on the temperature increase in the particle and would be fed into a computer which, in turn, would control the high frequency generator and make it possible to precisely control the increase in the intracellular increment of heat.

Magnetic susceptibility is measured by the ratio of the intensity of magnetization produced in a substance to the magnetizing force or intensity of the field to which it is subjected. This magnetic characteristic is routinely measured by magnetometer devices and is known to be temperature dependent; that is, it varies with the temperature. Thus, by taking particles and by measuring their magnetic susceptibility at various known temperatures, within the range of those temperatures expected to be used intracellularly, it is quite simple to calibrate the magnetometer equipment so that when it measures a magnetic characteristic of the particles intracellularly, a simple calibration will indicate the exact corresponding temperature of the particle.

EXAMPLE

The magnetic susceptibility of iron oxide varies with temperature as follows:

| TEMPERATURE | MAGNETIC SUSCEPTIBILITY IN CENTIMETER-GRAMS-SECOND ELECTROMAGNETIC UNITS (c.g.s.u.) |
| --- | --- |
| 28° Centigrade | $7120 \times 10^{-6}$ |
| 32° Centigrade | $7080 \times 10^{-6}$ |
| 36° Centigrade | $7040 \times 10^{-6}$ |
| 40° Centigrade | $7000 \times 10^{-6}$ |
| 44° Centigrade | $6960 \times 10^{-6}$ |
| 48° Centigrade | $6920 \times 10^{-6}$ |

Having established the magnetic susceptibility for corresponding temperatures it follows that by measuring the magnetic susceptibility, the corresponding temperature can be determined by calibration and interpolation. For example, if the measurement of magnetic susceptibiity were $6960 \times 10^{-6}$ c.g.s.u., it would indicate a temperature of 44°0 C. and if the measurement of magnetic susceptibility were $6940 \times 10^{-6}$ c.g.s.u., it would indicate a temperature of 46° C.

Another important feature of the present invention is that in addition to its usefulness in furnishing data on a three dimensional scale for the entire body, it can also be used with special techniques for selectively directing the particles to specific area or organs by the use of antigens, antibodies, or enzymes and thereby furnish data relevant to other disorders, ailments, and/or diseases.

There are many variations to the invention as described and this invention should be limited solely by the scope of the following claims.

I claim:

1. A process for the measurement of the intracellular temperature of cells within the body comprising: intracellularly injecting into the patient, minute particles capable of magnetic characteristics and of the size less than 1 micron to permit absorbing said minute particles into the cells, determining the magnetic susceptibility of the intracellular particles with magnetic susceptibility measuring equipment and correlating the determined magnetic susceptibility to a corresponding temperature of the particles.

2. The process of claim 1 wherein the particles are ferromagnetic, paramagnetic, or diamagnetic.

3. The process of claim 1 wherein the particles are selected from the group consisting of ferric hydroxide and iron oxide.

4. The process of claim 1 including providing a cancer cell seeking agent in a concentration sufficient to combine with and selectively direct the particles to the cancer cell.

5. The process of claim 1 wherein said particles are selectively directed to specific areas by the use of antigens, antibodies, or enzymes.

6. The process of claim 1 wherein the determined magnetic susceptibility is incorporated in a three dimensional scanning technique.

7. The process of claim 6 wherein the determined magnetic susceptibility is computerized and restructured in a three dimensional temperature model.

8. The process of claim 1 wherein the magnetic susceptibility is determined while a high frequency electromagnetic field is interrupted.

9. A process for the measurement of the intracellular temperature of cells within the body comprising:
   intracellularly injecting into the patient, minute magnetizable particles of the size less than 1 micron,
   absorbing said minute particles intracellularly into the cells,
   subjecting the patient to a stationary magnetic field so as to magnetize said particles,
   measuring the magnetization of the particles, and
   correlating these measurements to specific magnetic readings which have been calibrated to specific temperatures of the particles.

* * * * *